United States Patent [19]

Warriner

[11] Patent Number: Plant 5,341

[45] Date of Patent: Nov. 20, 1984

[54] ROSE PLANT JACAL

[75] Inventor: William A. Warriner, Tustin, Calif.

[73] Assignee: Jackson & Perkins Company, Medford, Oreg.

[21] Appl. No.: 475,163

[22] Filed: Mar. 14, 1983

[51] Int. Cl. ..... A01H 5/00

[52] U.S. Cl. ..... Plt./20

[58] Field of Search ..... Plt./20

*Primary Examiner*—Robert E. Bagwill

*Attorney, Agent, or Firm*—Klarquist, Sparkman, Campbell, Leigh & Whinston

[57] ABSTRACT

A hybrid tea rose variety having upright plant, large flowers of orange-red color which darken upon exposure to sunlight, large prickles, dark red new foliage, and little or no fragrance.

1 Drawing Figure

This present invention relates to a new and distinct variety of rose plant of the hybrid tea class which was originated by me by crossing the variety Spellbinder with the variety Futura.

The primary objective of this breeding was to product a new rose variety combining the color changing characteristic of Spellbinder with the deeper color of Futura. This objective was substantially achieved along with other desirable improvements as evidenced by the following unique combination of characteristics which are outstanding in the new variety and which distinguish it from its parents, as well as from all other varieties of which I am aware:

1. An upright plant similar to variety Spellbinder, but larger.
2. Large flowers of an orange-red color, similar to Royal Horticultural Society Colour Chart 42A which darkens upon two or three days' exposure to sunlight to a red similar to RHS 45A.
3. Large brown prickles, hooked downward.
4. Dark, reddish new foliage, close to RHS Grayed Purple, 183A.
5. Little or no fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:
- *Seed parent.*—Spellbinder.
- *Pollen parent.*—Futura.

Classification:
- *Botanical.*—Rosa hybrid.
- *Commercial.*—Hybrid tea.

FLOWER

Observations made from specimens grown at Irvine, Calif. in October.

Blooming habit: Recurrent, continuous.

Bud:
- *Size.*—1" To 1¼" when petals start to unfurl.
- *Form.*—Blunt top, broad base.
- *Color.*—When sepals first divide, Red 45C. When half blown; upper side of petals Red 48B on distal portion, near 47C in proximal portion; lower side of petals Red 48D.
- *Sepals.*—Color; Outer surface Green 138A heavily overlaid with Greyed Purple 183A. Three appendaged sepals lightly appendaged. Two unappendaged sepals hairy edged.
- *Receptacle.*—Color: Greyed Purple 183A. Shape: Apple. Size: Large. Surface: Smooth.
- *Peduncle.*—Length: Medium. Surface: Prickly. Color: Bronzy. Strength: Stiff, erect.
- *Opening.*—Petals fold out with very little curling.

Bloom:
- *Size.*—Large. Average open size: 5".
- *Borne.*—Singly.
- *Stems.*—Long, strong.
- *Form.*—When first open, high center. Permanence: Retains its form to the end.
- *Petalage.*—Number of petals under normal conditions: 30–35.
- *Color.*—Center of flower: Upper side of petals Red 42A; reverse side of petals Red 48D; base of petals Yellow 13A at point of attachment. General tonality from a distance Red 42A.
- *Variegations.*—None.
- *Discoloration.*—General tonality at end of first day: No change. Third day: Gradual darkening when exposed to sunlight to Red 45A.
- *Fragrance.*—Slight.

Petals:
- *Texture.*—Thick.
- *Shape.*—Round.
- *Form.*—Flat.
- *Arrangement.*—Imbricated. Petaloids in center, few.
- *Persistence.*—Drop off cleanly.
- *Lastingness.*—On the plant, long. As cut flower, long.

PLANT

Form: Bush.

Growth: Vigorous, upright.

Foliage: Number of leaflets on normal mid-stem leaves: usually 7.

*Size.*—Medium.
*Quantity.*—Normal.
*Color.*—New foliage: Greyed Purple 183A. Old foliage: Green 131A.

Leaflets:
*Shape.*—Oval.
*Texture.*—Upper side: Leathery.
*Edge.*—Serrated.
*Serration.*—Single, small.
*Petiole.*—Rachis: Color: Reddish. Underside: Prickels.
*Disease resistance.*—Resistant to mildew under normal growing conditions at Irvine, Calif.

Wood:
*New wood.*—Color: Greyed Purple 183A. Bark: Smooth.
*Old wood.*—Color: Green with brown shading. Bark:

Prickles:
*Quantity.*—On main stalks from base, many. On laterals from stalk, many.
*Form.*—Long, hooked downward.
*Color when young.*—Brown.
*Position.*—Irregular.

Small prickles:
*Quantity.*—On main stalks, few. On laterals, few.
*Color.*—Brown.

I claim:

1. A new and distinct variety of rose plant of the hybrid tea class, substantially as herein shown and described, characterized particularly as to novelty by the unique combination of its upright bush, orange-red flowers aging darker, numerous thorns, reddish new foliage and lack of fragrance.

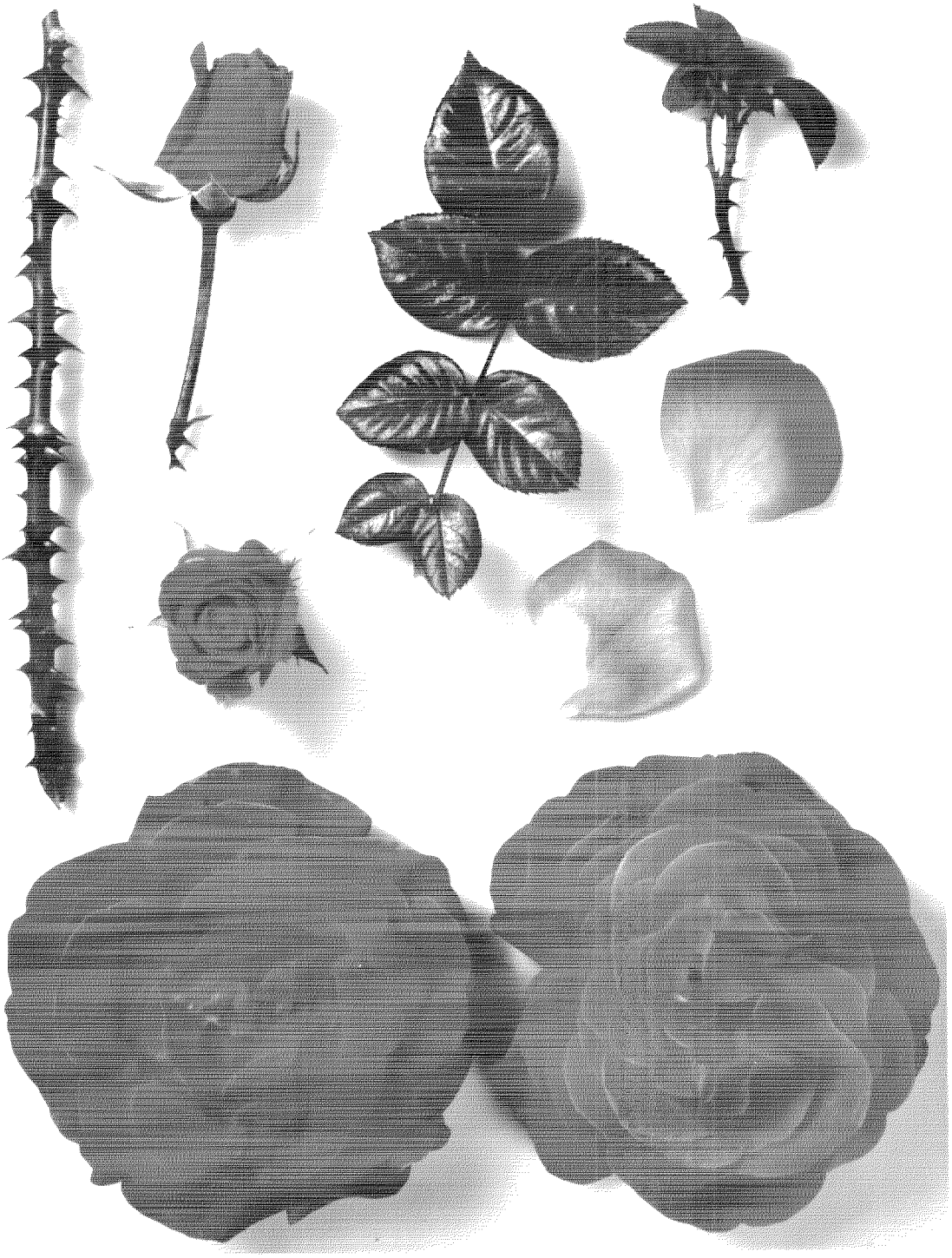

* * * * *